United States Patent

Hammond et al.

Patent Number: 5,369,093
Date of Patent: Nov. 29, 1994

[54] LIPOPEPTIDE DERIVATIVES

[75] Inventors: Milton L. Hammond, Somerville; James M. Balkovec, North Plainfield; David J. Mathre, Edison, all of N.J.

[73] Assignee: Merck & Co., Inc., Rahway, N.J.

[21] Appl. No.: 670,604

[22] Filed: Mar. 15, 1991

[51] Int. Cl.$^5$ .................. A61K 37/02; C07K 7/06; C07K 5/12
[52] U.S. Cl. ........................... 514/11; 514/9; 530/317
[58] Field of Search .............. 530/317; 514/9, 11

[56] References Cited

U.S. PATENT DOCUMENTS

| | | | |
|---|---|---|---|
| 3,892,726 | 7/1975 | Ondetti et al. | 530/328 |
| 4,287,120 | 9/1981 | Abbott et al. | 530/317 |
| 4,288,549 | 9/1981 | Breck et al. | 435/119 |
| 4,293,490 | 10/1981 | Abbott et al. | 530/317 |
| 4,293,491 | 10/1981 | Debono et al. | 530/37 |
| 4,320,054 | 3/1982 | Abbott et al. | 530/317 |
| 4,791,100 | 12/1988 | Kramer et al. | 514/12 |
| 4,965,343 | 10/1990 | Felix et al. | 530/328 |
| 5,021,341 | 6/1991 | Giacobbe et al. | 435/71.1 |

FOREIGN PATENT DOCUMENTS

| | | |
|---|---|---|
| 032009 | 7/1981 | European Pat. Off. |
| 0405997 | 1/1991 | European Pat. Off. |
| 2050385A | 1/1981 | United Kingdom |

OTHER PUBLICATIONS

Traber et al., Helv. Chim. Acta 62, 4, 1252–67 (1979).
Pache, W. et al., 13th International Congress Chemotherapy (1983), PS 4.8/3, Part 115, Abstract No. 10; also references in Ann. Reports in Med. Chem. 19, Sec. III, 130–131.

Primary Examiner—Robert J. Hill, Jr.
Assistant Examiner—S. G. Marshall
Attorney, Agent, or Firm—Elliot Korsen; Mark R. Daniel; Joseph F. Di Prima

[57] ABSTRACT

The present invention is directed to water-soluble derivatives of antibiotic lipopeptides having the formula.

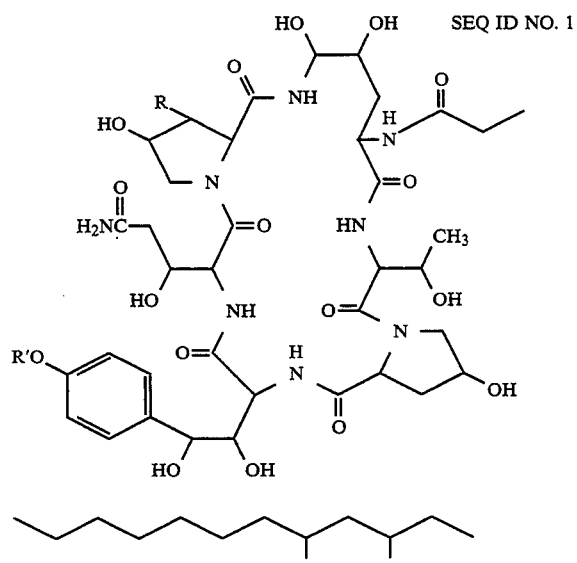

SEQ ID NO. 1 wherein R is H or OH and R' is a phosphono, sulfo or acyl radical possessing a charged group at neutral pH.
The derivatives are esters but having a charged group, have good solubility properties in aqueous medium, rendering them more useful as therapeutic agents.

9 Claims, No Drawings

LIPOPEPTIDE DERIVATIVES

The present invention is directed to a compound having the formula

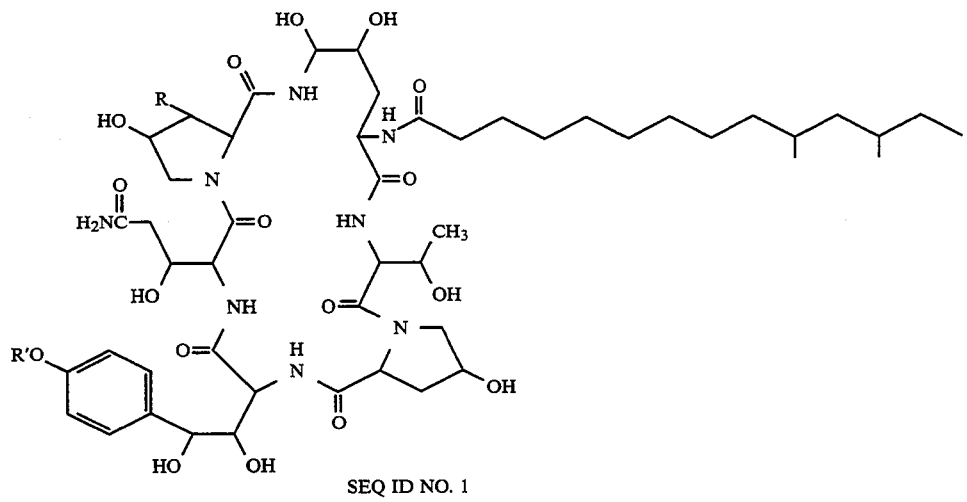

SEQ ID NO. 1

In this and succeeding formulas, R is H or OH, and R' is a phosphono, sulfo or acyl radical possessing a charged group at neutral pH.

"Phosphono, sulfo or acyl radicals which possesses a charged group at neutral pH" include those in which the charged group may be an anion form of an acid group or a cation form of an amino present on the group on the acyl radical. These radicals may be further defined as follows:

(1) By "phosphono" is meant a radical or group derived from and remaining after an OH of the phosphoric acid or monoester of phosphoric acid has reacted with the hydrogen of the phenolic group on the lipopeptide and may be represented by —PO$_3$AH wherein A is H, C$_1$–C$_6$ alkyl, phenyl or substituted phenyl in which the substituent is alkyl, alkyloxy, alkylthio, or alkylamino, or a cation salt thereof;

(2) By "sulfo" is meant a radical or group derived from and remaining after an OH of the sulfuric acid has reacted with the hydrogen of the phenolic group on the lipopeptide and may be represented by —SO$_3$H or cation salt thereof;

(3) By "acyl" is meant a radical or group derived from a carboxylic acid and further defined as follows:

(i) COC$_n$H$_{2n}$CO$_2$H wherein n is 1 to 6, or a cation salt thereof;

(ii) CONAC$_n$H$_{2n}$CO$_2$H wherein A is as defined in (1) and n is 1 to 6, or a cation salt thereof;

(iii) COOC$_n$H$_{2n}$CO$_2$H wherein n is 1 to 6, or a cation salt thereof;

(iv) CONA(CHB)CO$_2$H wherein A is as defined in (1) and B is a residue of an amino acid, or a cation salt thereof;

(v) COCHBNR$_1$R$_2$ wherein B is a residue of an amino acid, R$_1$ and R$_2$ independently are H, C$_1$–C$_6$ alkyl, or phenyl, or an acid addition salt thereof;

(vi) CONAC$_n$H$_{2n}$NR$_1$R$_2$ wherein A is as defined in (1), R$_1$ and R$_2$ independently are as defined in (v), n is 2 to 6, or an acid addition salt thereof;

(vii) COOC$_n$H$_{2n}$R$_1$R$_2$ wherein R$_1$ and R$_2$ independently are as defined in (v), n is 2 to 6, or an acid addition salt thereof;

(viii) COC$_n$H$_{2n}$NR$_1$R$_2$ wherein R$_1$ and R$_2$ independently are as defined in (v), n is 1 to 6 or an acid addition salt thereof; and (ix) COX where X is a leaving group;

A "leaving group" is, as generally recognized in organic chemistry, a conjugate base of a strong acid. Representative leaving groups include ions such as chloride, bromide, iodide, bisulfate, methyl sulfate, benzenesulfonate, p-toluenesulfonate, methanesulfonate, dibenzylphosphate, p-nitrophenoxide, pentafluorophenoxide, trichlorophenoxide, and the like.

The preferred group for R is

or a cation salt thereof.

By "cation salt" is meant a salt of Li, K, Mg, Na, Ca, and (C$_1$–C$_4$alkyl)ammonium. The salt may form on one or both of the hydroxyls of the phosphono group.

By "acid addition salt" is meant pharmaceutically acceptable salts such as hydrochloride, sulfate, phosphate, salicylate, lactate, isethionate, hydrobromide, maleate, citrate, tartrate, acetate, succinate and the like. Suitable acid addition salts and cation salts may be found in a review article by S. M. Berge et al., J. Pharmaceutical Sciences 66, 1 (1977).

By "neutral pH" is meant pH 6–8.

The preferred compounds are those in which R' is phosphono and which may be represented by formula IA-P and IB-P, or salts thereof.

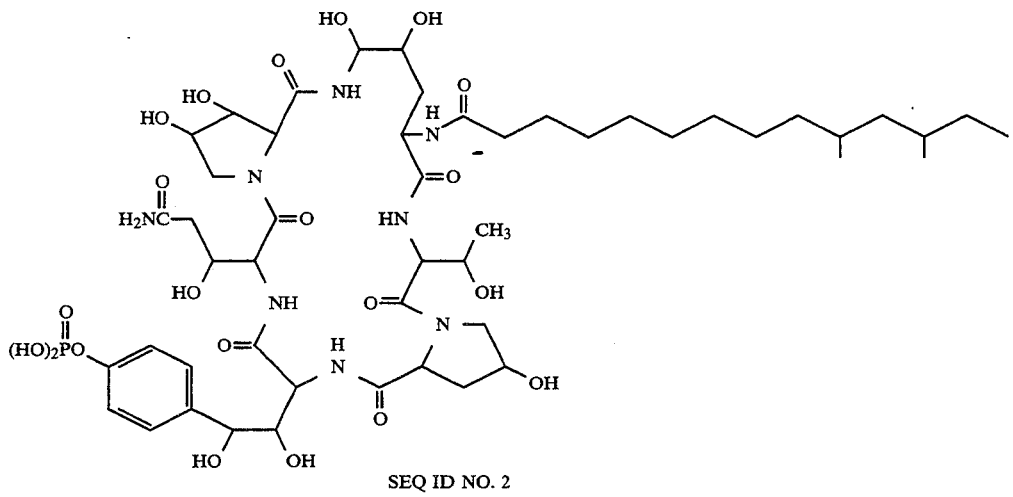

(IA-P)

SEQ ID NO. 2

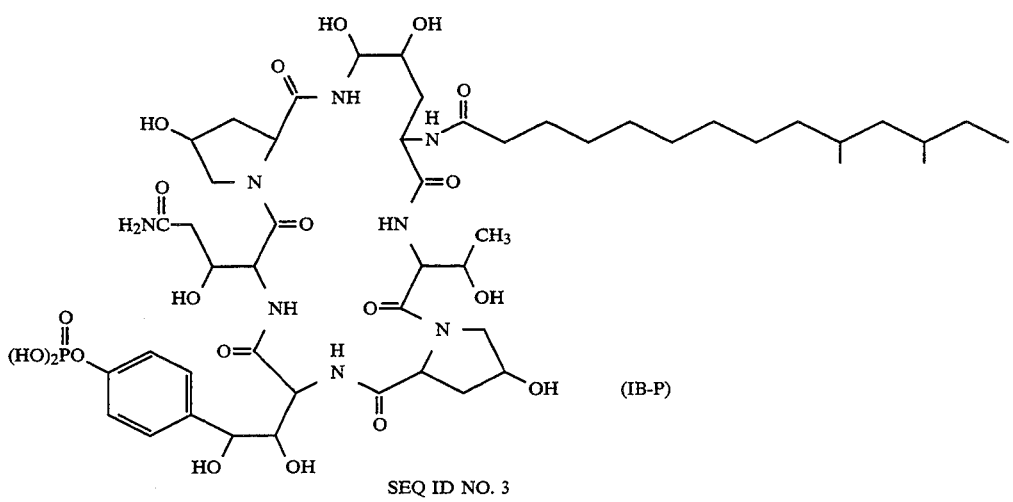

(IB-P)

SEQ ID NO. 3

The compounds of the present invention may be used as antifungal and antiprotozoal agents. As antifungal agents, they may be used for the control of both filamentous fungi and yeasts. Among the filamentous fungi which may be controlled are *Aspergillus* species such as *Aspergillus flavus, Aspergillus fumigatus, Neurospora* species, *Fusarium* species, *Alternaria* species, and *Cochliobolus miyabeanus* and the like. They also may be used for the treatment of mycotic infections, especially those caused by the *Candida* organisms such as *C. albicans, C. parapsilosis* and the like. As antiprotozoal agents they may be useful for the control of organisms causing amebiasis such as *Entamoeba histolytica*, or malaria such as *Plasmodium* species, or other organisms such as *Trypanosoma* species, *Toxaplasma* species, *Cryptosporidia* and the like. They are especially useful for the prevention and or treatment of *Pneumocystis carinii* infections to which immune compromised patients are especially susceptible.

The compounds of the present invention which are generally white or light colored solids are derivatives of antibiotic lipopeptides. Unlike the parent compounds, the present compounds have good solubility properties in water and aqueous media, usually hundredfold or more. This property renders the compounds of the present invention more useful as therapeutic agents than the parent compound in many applications. For example, they are adaptable to being used more readily in injectibis compositions. Moreover, the compounds may have a prolonged duration of action.

The compounds of the present invention may be prepared from a lipopeptide having the formula (Z) by selectively esterifying at the phenolic hydroxyl and forming an ester link according to the following equation:

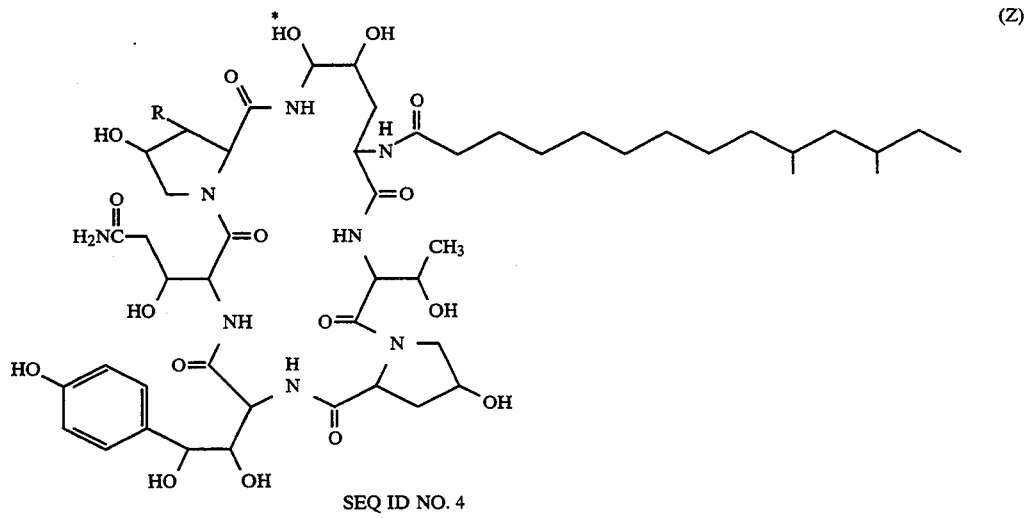

(Z)

SEQ ID NO. 4

The lipopeptides which are starting materials for Compounds IA-P and IB-P are naturally occurring and may be represented respectively as Compounds ZA and ZB.

compound which would be embraced in the formula using the aforecited definitions for R' and for X.

Since R' must have an ionizable group, the ionizable group generally is first protected prior to the esterifica-

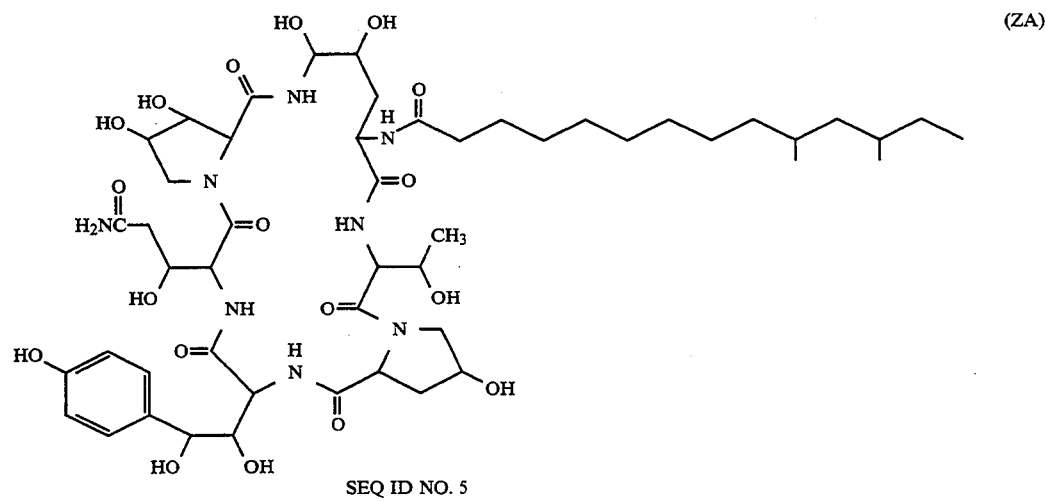

(ZA)

SEQ ID NO. 5

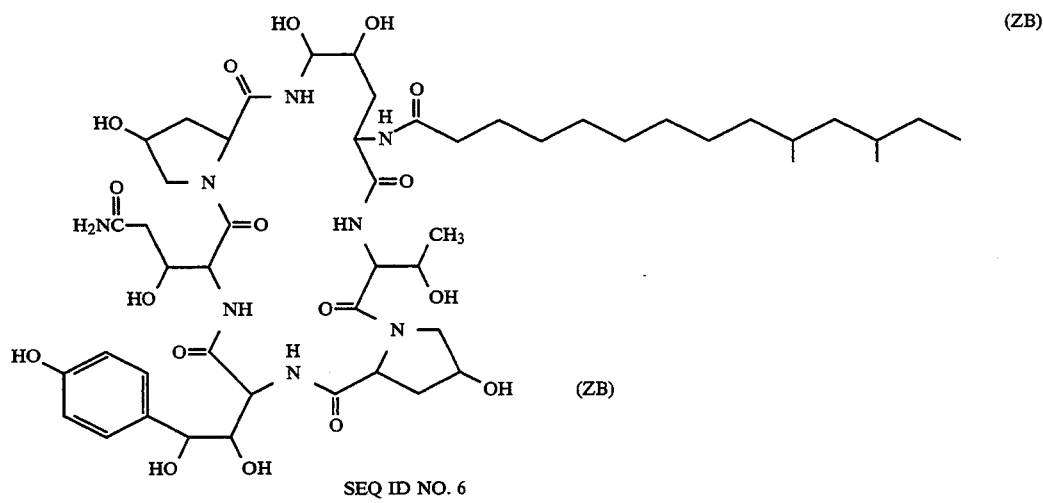

(ZB)

SEQ ID NO. 6

R'X is an ester forming compound which has within the R' structure an ionizable groups and may be any tion step and the protecting group removed after completion of the esterification step.

Also, the OH group in structure (Z), indicated with an asterisk (*) is oftentimes protected during the acylation (ester formation). Thus, the preparation of the desired products of the present invention may entail at least one protection/deprotection step.

Generally, carrying out the preparation of Compound I, the first step is the etherification of the starting material, Compound Z, to form an ether at the indicated OH group resulting in Compound Z'. The ether of the lipopeptide (Z') then is esterified to produce an ester product in which both the OH of the lipopeptide and the ionizable group in the ester are protected (Z''). The protecting groups are conveniently removed by hydrogenation to obtain the product of the present invention. The foregoing may be seen in the following reaction scheme according to steps (1), (2') and (3').

When in Compound I, R is equal to a phosphono group, an alternative and preferred process is direct phosphorylation without the need for protecting the asterisked OH group and proceeding therefore according to step (2) in the reaction scheme and forming Compound Z''' as subsequently more fully detailed.

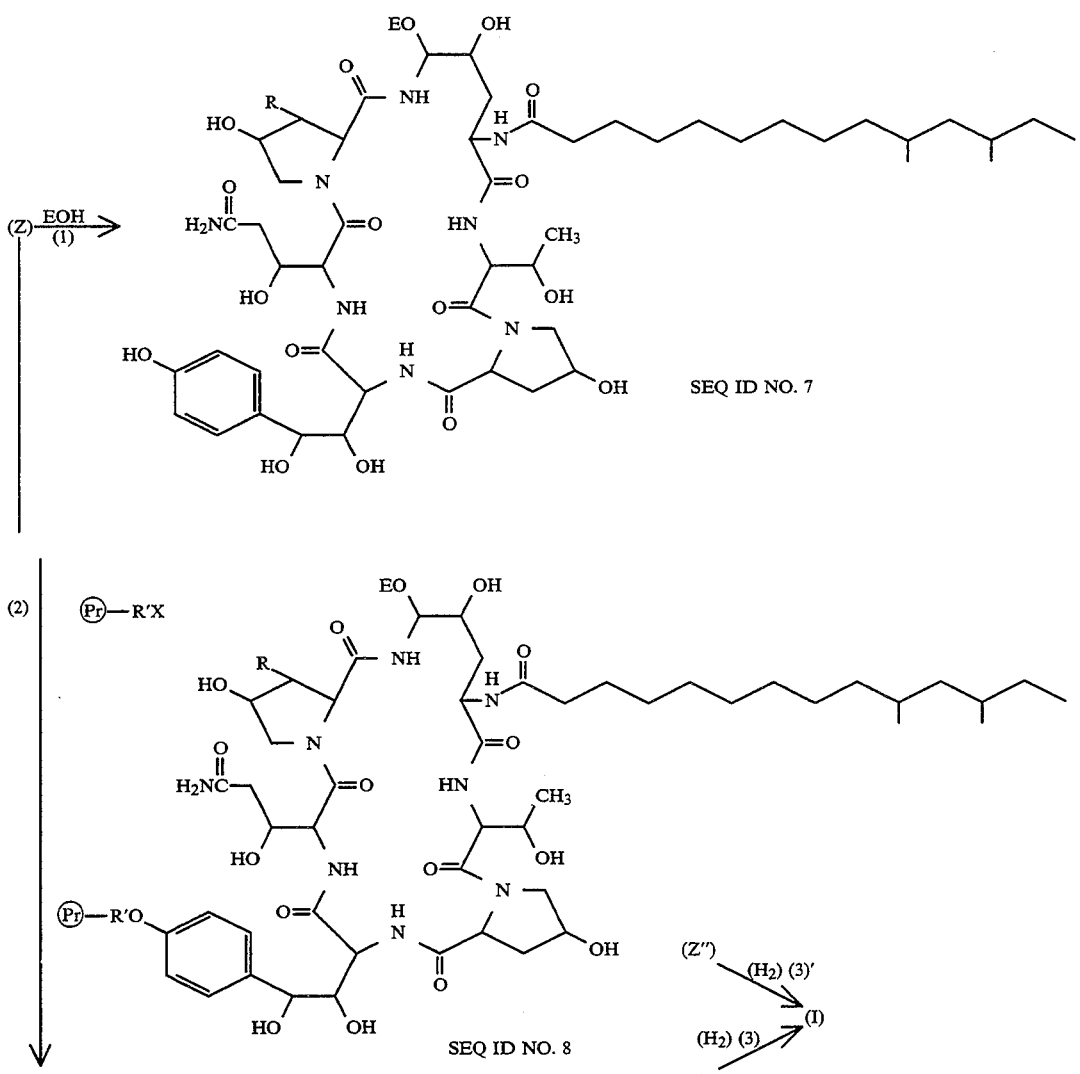

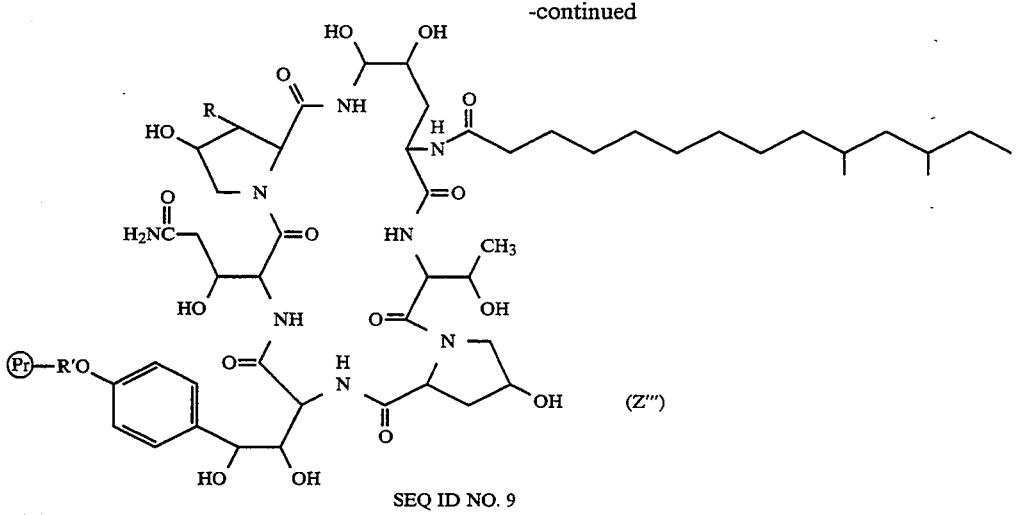

(Z''')

SEQ ID NO. 9

The Pr in Pr—R'X represents a protecting group for the ionizable group. Since the ionizable group is frequently a hydroxyl group or an amino group, the protecting group for hydroxyl may be a group such as benzyl and for amino, a group such as benzyloxycarbonyl, which are conveniently removed by hydrogenation.

For carrying out Reaction (1), in the above scheme, EOH is conveniently benzyl alcohol although other ether forming and readily cleavable alcohols may be employed, such as p-methoxybenzyl alcohol and 2,2,2-trichloroethanol.

The ether formation may be carried out by adding benzyl alcohol or other suitable alcohol and p-toluenesulfonic acid to a solution or dispersion of the lipopeptide in a solvent and stirring at room temperature for from about 16 to 26 hours. The volatiles are then removed in vacuo and the intermediate (Z') ether product obtained as residue. The latter may be purified by preparative high performance liquid chromatography (HPLC).

The resulting ether (Z') may be employed in the esterification. The esterification may be carried out by first adding dropwise with stirring a solution of lithium hydroxide to a dimethylformamide solution of the appropriate lipopeptide or ether of the lipopeptide and PR—R'X. The resulting mixture stirred for 1 to 20 hours. The volatiles are then removed in vacuo to obtain the crude Pr—R' ester of the lipopeptide (Z''') or of the ether of the lipopeptide (Z'') as a residue. The latter (Z'' or Z''') is then purified by preparative performance liquid chromatography (HPLC) using H₂O/CH₃CN as eluting agent. The eluate fractions having the desired retention time are lyophilized to obtain the desired intermediate ester (Z'') or (Z''').

The preferred derivatives of the lipopeptides are phosphate esters. When the ester is a phosphate ester, the preferred esterification intermediate is a dibenzyl phosphate ester. The dibenzyl phosphate ester may be prepared by adding a solution of lithium hydroxide in dimethylformamide to a stirred mixture of lipopeptide or benzyl ether of lipopeptide and tetrabenzyl pyrophosphate to obtain the dibenzyl phosphate ester of the lipopeptide.

The acid or acid salt of the ester (I) where R is phosphono may be obtained by low pressure hydrogenolysis of the dibenzyl phosphate ester of the lipopeptide or of the benzyl ether of the lipopeptide. During hydrogenolysis both the benzyl of the phosphate ester and the benzyl of the benzyl ether are cleaved to obtain a phosphate ester of the lipopeptide.

If it is desired to obtain the ultimate ester as its water-soluble salt, the hydrogenolysis may be carried out under mildly alkaline conditions and the desired product recovered as its salt. The free acid may be recovered from the salt by controlled acidification. In some cases, the salt is preferably prepared after first obtaining the free acid and reacting the acid with an appropriate base.

In one preferred method of carrying out the hydrogenolysis, a solution of dibenzyl phosphate in aqueous ethanol is hydrogenated at 1 atmosphere over Pd-C catalyst for 10 to 20 hours whereupon the benzyl groups of the phosphate ester are removed to obtain Compound I as an acid. If the starting lipopeptide is benzyl ether, the benzyl of the ether is also removed.

When it is desired to obtain the ultimate ester product as a salt of the acid, the hydrogenolysis medium may be made mildly alkaline with alkali metal bicarbonate and the salt recovered directly. Alternatively, the free acid may be recovered on hydrogenolysis and subsequently converted to the salt by methods known in the art including simply contacting the free acid with the base supplying the desired cation and evaporating the solution to dryness.

When R' is a sulfuric acid ester or carboxylic acid ester, the reaction may be carried out in a manner similar to that described for phosphoric acid esters. R may also be a radical in which the charged group at a neutral pH is an ammonium group formed preferably from the amino group of an amino acid, the carboxyl group of which has been esterified at the phenolic hydroxyl.

In certain instances the preferred R may be a sulfate ester. In these cases the sulfate ester may be prepared directly by treatment of a solution of the lipopeptide or lipopeptide benzyl ether in pyridine with sulfur trioxide pyridine complex to produce the pyridinium sulfate ester. If the free acid is desired it may be obtained by acidification with a strong acid such as hydrochloric acid followed by purification using a "ZORBAX" (DuPont) C8 reverse phase HPLC column as the stationary phase. If the lipopeptide benzyl ether is employed, the ether benzyl may be removed by hydrogenolysis as described above.

When RX is a carboxylic acid derivative the preferred reagents for acylation are the carboxylic acid chlorides and anhydrides. The incipient charged group if it is to be a carboxylic acid salt preferably may be protected during the acylation reaction as a benzyl ester or other easily removed ester groups such as 2,2,2-trichloroethyl ester or allyl ester. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in one preferred esterification, the lipopeptide or lipopeptide benzyl ether in pyridine containing 4-dimethylaminopyridine as catalyst is treated with the symmetrical anhydride of the carboxylic acid to produce the carboxylic ester. Deprotection, preferably by hydrogenolysis of the benzyl ester, if the charged group is to be an acid, or by hydrogenolysis of the benzyloxycarbonyl group if the charged group is to be an amine, releases the carboxylic acid or the amine respectively. If the charged group is to be an acid then the hydrogenolysis may be carried out under mildly alkaline conditions to obtain the water-soluble salt directly. Conversely, if the charged group is to be amine base the hydrogenolysis may be carried out under mildly acidic conditions to obtain the water soluble ammonium salt directly.

In certain instances such as in radical groups (3ii), (3iv), and (3vi) above, the ester linkage forms a portion of a carbamate. In those groups when A (as defined in radical group (1) above) is hydrogen, the preferred reagent for acylation is isocyanate. The incipient charged group if it is to be a carboxylic acid salt preferably may be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the amine group may include t-butoxycarbonyl or 2,2,2-trichloroethoxycarbonyl or other protecting groups well known to those skilled in the art. Thus, in a preferred esterification, the lipopeptide or lipopeptide benzyl ether in pyridine containing 4-dimethylaminopyridine is treated with the isocyanate to produce the carbamate. Deprotection may then proceed in a preferred case by hydrogenolysis as described above to release the charged group.

In those groups in which A (as defined in radical group (1)) is other than hydrogen, a different procedure must be used. In these cases a preferred method involves initial formation of a reactive carbonate. Thus, a solution of the lipopeptide or benzyl ether in dimethylformamide containing lithium hydroxide is treated with bis(p-nitrophenyl) carbonate and in this way the mixed p-nitrophenyl carbonate is prepared. In a separate step, the p-nitrophenyl carbonate is converted to the desired carbamate. Treatment of the mixed p-nitrophenyl carbonate in dimethylformamide with a secondary amine provides the protected carbamate. Deprotection may then proceed in a preferred case by hydrogenolysis as described above to unveil the charged group and provide the compounds described in radical group (3ii), (3iv) and (3vi) above where A is other than hydrogen.

When compounds such as those described in radical group (3iii) and (3vii) above are desired, the ester link forms a portion of a carbonate. In these cases, the preferred reagents for acylation are the chloroformates. The incipient charged group if it is to be a carboxylic acid salt preferably may be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other groups well known to those skilled in the art. Thus, in a preferred esterification, the lipopeptide or lipopeptide benzyl ether in pyridine containing 4-dimethylaminopyridine is treated with the chloroformate to produce the carbonate. Deprotection may then proceed in a preferred case by hydrogenolysis as described above to release the charged group.

Many compounds of the present invention are useful for inhibiting or alleviating *Pneumocystis carinii* infections. In such use, Compound I or a composition containing Compound I may be administered in a therapeutically effective or inhibitory amount to subjects infected with or susceptible to being infected with *Pneumocystis carinii*.

The suitability of the compounds of the present invention for therapeutic or anti-infective purposes may be determined in studies on immunosuppressed rats when Sprague-Dawley rats (weighing approximately 250 grams) are immunosuppressed with dexasone in the drinking water (2.0 mg/L) and maintained on a low protein diet for five weeks to induce the development of pneumocystis pneumonia from a latent infection. Before drug treatment, two rats are sacrificed to confirm the presence of *Pneumocystis carinii* pneumonia (PCP). Six rats (weighing approximately 150 grams) then are injected twice daily for four days intravenously (I.V.) via the tail vein with Compound IA-P in 0.25 ml of vehicle (distilled water). A vehicle control is also carried out. All animals continue to receive dexasone in the drinking water and low protein diet during the treatment period. At the completion of the treatment, all animals are sacrificed, the lungs are removed and processed, and the extent of disease determined by microscopic analysis of stained slides.

A similar experiment may be carried out in which the rats are injected intraperitoneally (I.P.) twice daily for four days and then sacrificed, the lungs removed and processed, and the extent of disease determined by microscopic analysis of stained slides.

The compounds of the present invention are active against many fungi and particularly against *Candida* species. The antifungal properties may be illustrated with the minimum fungicidal concentration (MFC) and minimum inhibitory concentration (MIC) determinations against certain *Candida* organisms in a microbroth dilution assay carried out in a Yeast Nitrogen Base (Difco) medium with 1% dextrose (YNBD).

In carrying out such an assay, Compound IA was solubilized in 10% dimethyl sulfoxide (DMSO) and diluted to 2560 $\mu$g/ml. The compound was then diluted to 256 $\mu$g/ml in YNBD. 0.15 ml of the suspension was dispensed to the top row of a 96-well plate (each well containing 0.15 ml of YNDB) resulting in a drug concentration of 128 $\mu$g/ml. Two-fold dilutions were then made from the top row to obtain final drug concentrations ranging from 128 to 0.06 $\mu$g/ml.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of $1-5\times10^6$ colony forming units (CFU)/ml.

96-well microplates were inoculated using a MIC-2000 (Dynatech) which delivers 1.5 μl per well yielding a final inoculum per well of $1.5-7.5\times10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 μl samples from the wells in the 96-well microplate were transferred to a single well tray containing Sabouraud dextrose agar. The inoculated trays were incubated 24 hours at 28° C. and then read for MFC. MFC is defined as the lowest concentration of drug showing no growth or less than 4 colonies per spot.

When Compound IA-P was tested against three strains of Candida albicans, it showed both inhibitory and fungicidal properties with minimum inhibitory concentration ranging from 16 to 32 μg/ml and minimum fungicidal concentration from 4 to 128 μg/ml. On test against Candida tropicalis, the minimum inhibitory concentration was found to be 16 μg/ml and the minimum fungicidal concentration 64 μg/ml.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound I or one of the components. Concentrate compositions suitable for dilutions prior to use may contain 90% or more by weight. The compositions include compositions suitable for rectal, topical, parenteral (including subcutaneous, intramuscular, and intravenous), pulmonary (nasal or buccal inhalation), nasal administration, or insufflation. The compositions may be prepacked by intimately mixing Compound I with the components suitable for the medium desired.

When the compound is for antifungal use any method of administration may be used. For treating mycotic infection, oral administration is frequently preferred. When oral administration is to be employed, it may be with a liquid composition or a solid composition. For liquid preparations, the therapeutic agent is preferably formulated with water or aqueous compositions, but if desired, may be formulated with glycols, oils, alcohols, and the like. For solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The Compound I is preferably formulated in aqeuous therapeutic compositions for intravenous or intraperitoneal injection when use against Pneumocystis carinii is contemplated, and may be presented in unit dosage form in ampoules or in multidose containers, if necessary with an added preservative. The compositions may also take such forms as solutions in aqueous vehicles such as 0.85 percent sodium chloride or 5 percent dextrose in water, and may contain formulating agents such as stabilizing and/or dispersing agents. Buffering agents as well as additives such as saline or glucose may be added to make the solutions isotonic. The drug also may be solubilized in alcohol/propylene glycol or polyethylene glycol for drip intravenous administration. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 1000 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The preferred delivery system for inhalation is a metered dose inhalation (MDI) aerosol, which may be formulated as a solution of Compound I in suitable propellants, such as fluorocarbons or hydrocarbons.

Although the compounds of the present invention may be employed as tablets, capsules, topical compositions, insufflation powders, suppositories and the like, the advantage of the derivatives of the present invention over the parent lipopeptide is in their water solubility. Hence, the compounds of the present invention are most effectively utilized in injectibis formulations and also in liquid compositions suitable for aerosol sprays.

Compound I also may be employed against a broad spectrum of yeasts and filamentous fungi (molds). For non-medical application, the product of the present invention may be employed in compositions in an inert-carrier which includes finely divided dry or liquid diluents, extenders, fillers, conditioners and excipients, including various clays, diatomaceous earth, talc, and the like, various organic liquids such as lower alkanols, for example, ethanol and isopropanol, or kerosene, benzene, toluene and other petroleum distillate fractions or mixtures thereof. However, as with medical applications, the compounds are best utilized in aqueous compositions.

The following examples illustrate the invention but are not to be construed as limiting:

EXAMPLE 1

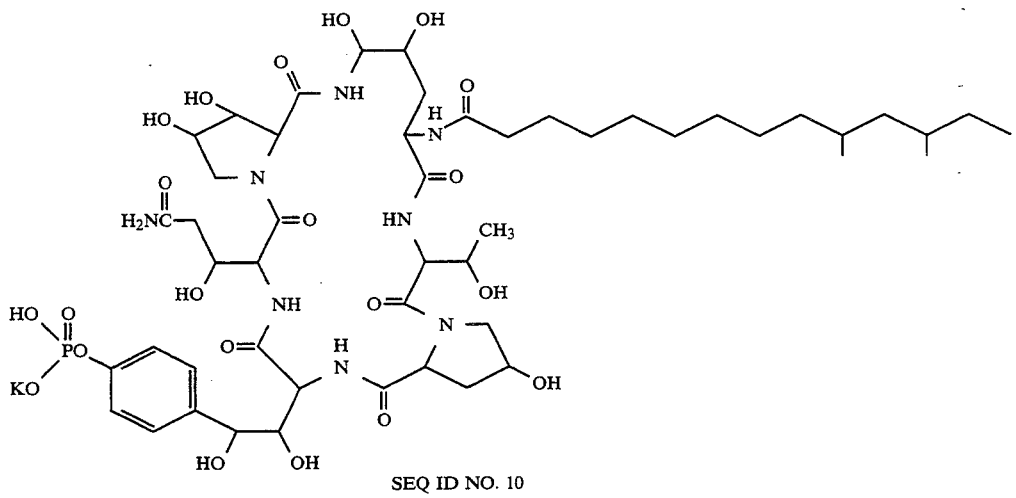

SEQ ID NO. 10 (1)

A. Preparation of dibenzyl phosphate intermediate

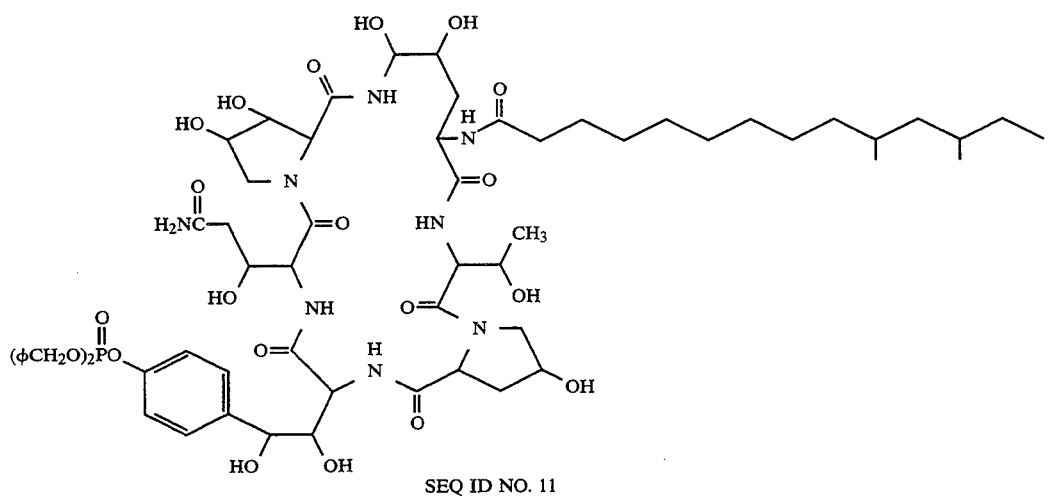

SEQ ID NO. 11 (Z'-1)

To a stirred, cooled (−15° C.) solution of 10.8 mg (10.0 μmol) of Compound ZA and 6.4 mg (11.9 μmol) of tetrabenzyl pyrophosphate in 1 milliliter of dry DMF was added dropwise 11 microliters (11 μmol) of 1.0 M aqueous lithium hydroxide over a 15 minute period. The solution was stirred for 3 hours at −15° C. and then allowed to warm to room temperature overnight to obtain the intermediate dibenzyl phosphate product in the reaction mixture. The reaction mixture was diluted into 10 milliliters of 50:50 ethanol/water and the dibenzyl phosphate intermediate adsorbed onto a 1×25 column packed with "AMBERCHROM"-161 (TosoHass, medium diameter divinylbenzene-polystyrene resin) at a rate of 1 mL/min. The column was then washed with 50 milliliters of 50:50 ethanol/water (1 mL/min) to remove the dibenzylphosphoric acid and dimethylformamide and the dibenzylphosphate intermediate eluted with 25 milliliters of 90:10 ethanol/water at 1 mL/min.

B. Hydrogenolysis of dibenzyl phosphate intermediate

The ethanol/water solution containing the intermediate dibenzyl phosphate was charged with 5 percent Pd/C (50 mg) and the resulting mixture stirred for 4 hours at room temperature under an atmosphere (1 atm) of hydrogen. The mixture was filtered through a pad of SOLKA-FLOC (cellulose based filter aid, James River Corp. of Virginia) to remove the catalyst. The filtrate was diluted with 75 milliliters of 10 mM aqueous $KH_2PO_4$ and the product adsorbed onto a 1×25 centimeter packed with "AMBERCHROM"-161. The column was washed with 75/25 water/ethanol to remove the salts and then eluted with 25:75 water/ethanol to recover the product. The solution was concentrated in vacuo to dryness. The residue was dissolved in absolute ethanol, then concentrated to dryness in vacuo three times to remove all the water and to obtain 9 mg of Compound IA, monopotassium salt (compound of formula (1)) as a white powder. $^{13}C$ NMR Chemical shifts ($CD_3OD$): δ 11.6, 19.7, 20.2, 20.7, 27.0, 28.0, 30.3, 30.6, 30.8, 31.18, 31.23, 32.9, 71.9 34.9, 36.7, 38.1, 38.4, 39.4, 45.9, 54.4, 51.2, 55.4 56.3, 57.1, 58.3, 62.5, 68.2, 65.9 70.7, 70.8, 71.3, 73.8, 75.9 76.1, 121.1, 121.3, 129.5, 138.4, 153.1, 169.5, 172.7, 173.2, 173.5, 174.5, 174.6, 175.9, 177.1.

EXAMPLE 2

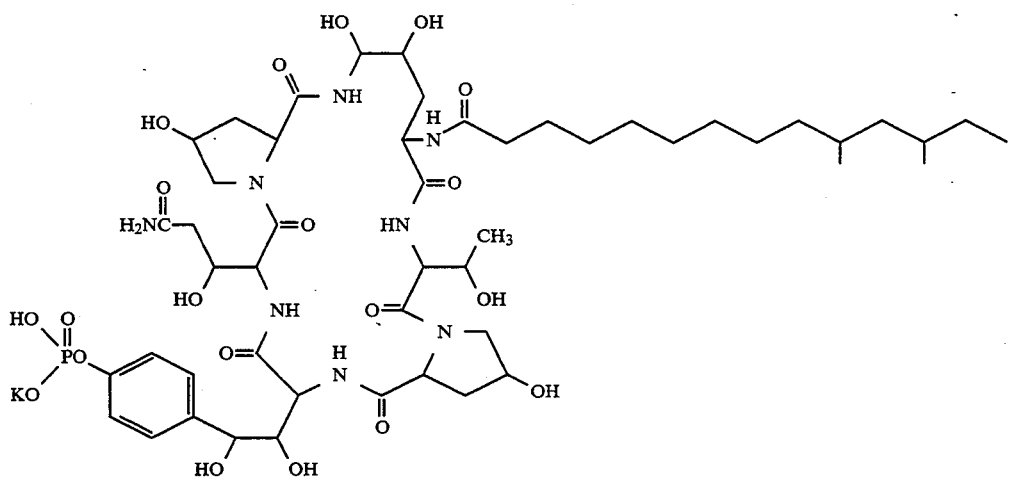

SEQ ID NO. 12

A. Preparation of Dibenzyl Phosphate Intermediate

In an operation carried out in a manner similar to that described in Example 1, 11 μL (11 μmol) of 1.0M aqueous lithium hydroxide was added dropwise to a stirred, cooled (−15° C.) solution of 10.6 mg (10.0 μmol) of Compound ZB and 6.4 mg (11.9 μmol) of tetrabenzyl pyrophosphate in 1 milliliter of dry dimethylformamide. The mixture was stirred for 3 hours at −15° C. then allowed to warm to room temperature overnight to obtain the intermediate dibenzylphosphate. It was then diluted into 10 milliliters of 50:50 ethanol/water and adsorbed onto 1×25 cm column of "AMBER-CHROM"-161 resin at 1 mL/min. The column was then washed with 50:50 ethanol/water and the dibenzyl phosphate intermediate eluted with 90:10 ethanol/water.

B. Hydrogenolysis of Dibenzyl Phosphate Intermediate

The ethanol/water solution containing the intermediate dibenzyl phosphate was hydrogenated in a manner similar to that described in Example 1 using 5 percent Pd/C (50 mg) 1 atmosphere of hydrogen. The mixture was filtered to remove the catalyst and the filtrate was diluted with 75 milliters of 10 mM aqueous $KH_2PO_4$. The aqueous solution was adsorbed onto a 1×25 cm column packed with "AMBERCHROM" 161 resin. The column was then washed with 75:25 water/ethanol and the product then eluted with 25:75 water/ethanol. The eluate was concentrated in vacuo to dryness (flushing three times with absolute ethanol) to obtain 8.5 mg of Compound IB, monopotassium salt (compound of formula (2)) as a white powder. $^{13}C$ NMR Chemical shifts ($CD_3OD$): δ 11.6, 19.8, 20.2, 20.7, 26.3, 28.1, 30.3, 30.6, 30.8, 31.14, 31.22, 32.9, 75.1 34.9, 36.7, 38.1, 38.8, 39.9, 45.9, 60.5 51.3, 55.6, 56.5, 57.1, 58.1, 61.2, 68.8, 60.8 70.6, 71.0, 71.1, 73.9, 39.1 75.5, 77.0, 121.3, 129.4, 137.3, 153.9, 170.7, 171.9, 172.6, 174.5, 176.1, 176.3, 176.4, 177.1.

EXAMPLE 3

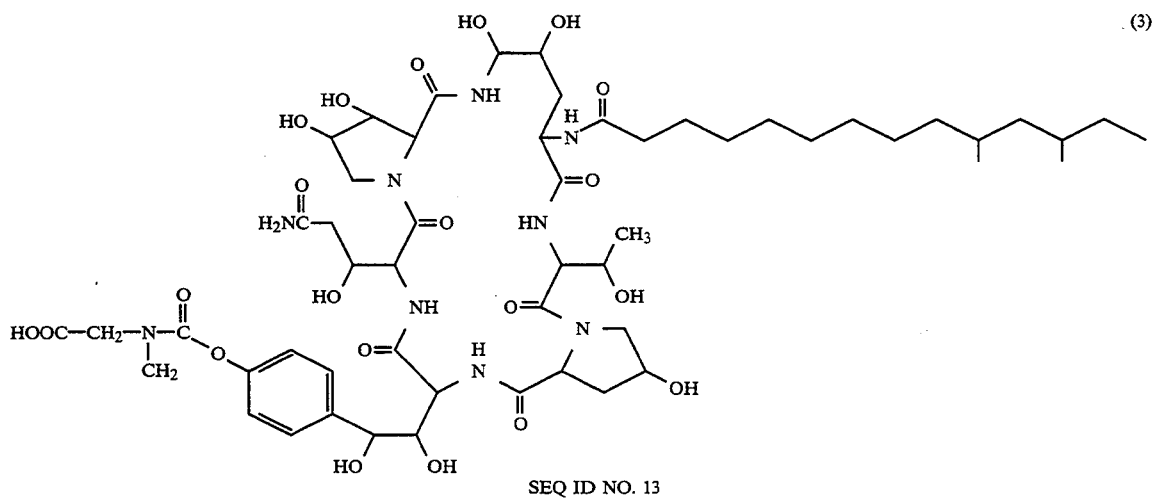

SEQ ID NO. 13

Part A. p-Nitrophenyl carbonate ester

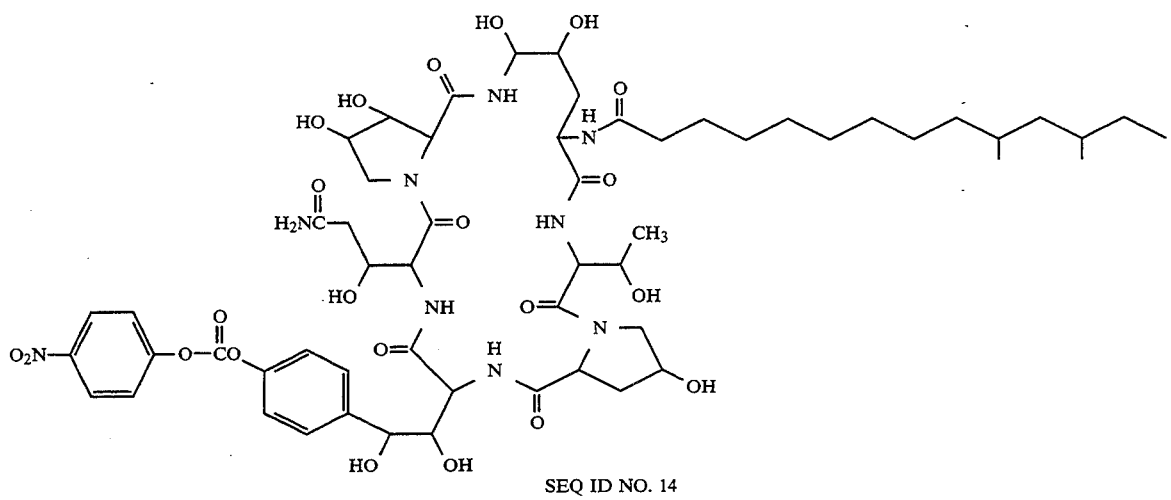

SEQ ID NO. 14

To a solution of ZA (0.350 g, 0.32 mmol) and bis(4-nitrophenyl)-carbonate (0.118 g, 0.38 mmol) in dimethylformamide (3 mL) at 0° C. is added 2N LiOH in three portions at 5 minute intervals (58 µL per portion, total of 0.35 mmol LiOH). Upon completion of the additions, the reaction mixture is allowed to stir for 5 minutes then warmed to room temperature and stirred for 3 hours. The reaction is then quenched with acetic acid (0.1 mL) and the mixture concentrated in vacuo and the residue dissolved in acetonitrile/water. The resulting solution is filtered and purified by preparative reverse phase chromatography, eluting with acetonitrile/water. The fractions containing the desired product are concentrated to remove the acetonitrile and then lyophilized to obtain the purified p-nitrophenyl carbonate ester.

Part B. Conversion to N-methylcarbamoyl Acetic acid derivative

To a solution of 100 mg (0.08 mmol) of the p-nitrophenyl carbonate prepared as described in Part H in 1 ml of dry dimethylformamide is added 15 mg (1.1 eq) of benzyl safcosine and the mixture allowed to stir at room temperature for 20 hours. The crude reaction mixture is concentrated in vacuo, the residue dissolved in water/acetonitrile and purified by reverse phase chromatography on "ZORBAX" C8 column and eluted with acetonitrile/water. The fractions containing the desired intermediate are concentrated in vacuo to remove the acetonitrile and then lyophilized to obtain a purified benzyl ester.

The ester is dissolved in 15 ml of absolute ethanol and to the solution is added 15 mg of 10% Pd-C and stirred at 1 atmosphere for 5 hours. At the end of this period, the mixture is filtered and the filtrate concentrated to obtain the desired product Compound of formula (3). The product is purified on preparative HPLC employing water/acetonitrile.

EXAMPLE 4

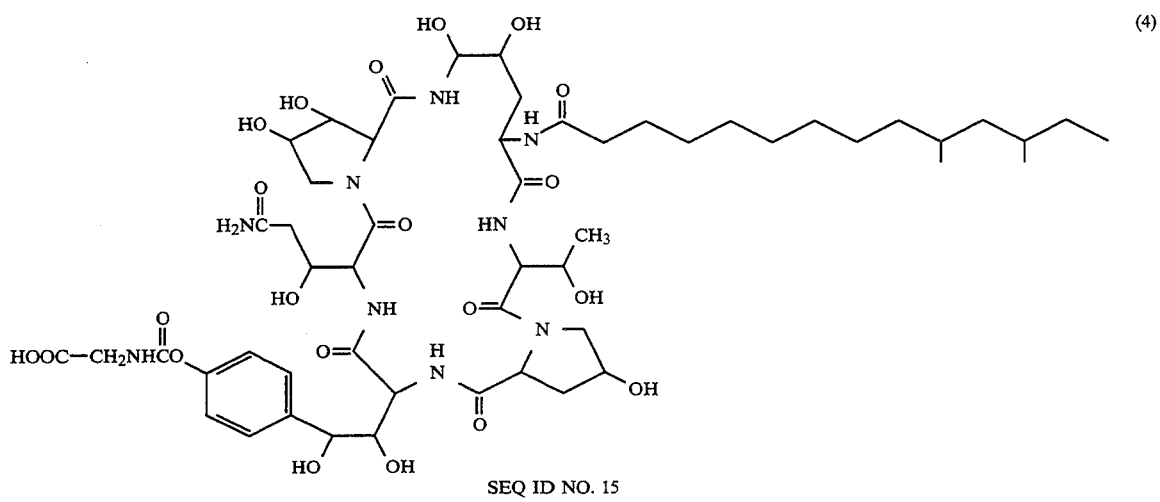

(4)

SEQ ID NO. 15

Part A. Preparation of Benzyl Ether 350 milligrams of Compound ZA is suspended in 7 milliliters of tetrahydrofuran and to the suspension is added 0.68 milliliter of benzyl alcohol and 7 milligrams of p-toluenesulfonic acid. The mixture remains heterogeneous; 3 milliliters of dimethylformamide is added and the resulting solution stirred for 24 hours at room temperature. At the end of this period, the volatiles are removed in vacuo to obtain a residue which is purified by preparative HPLC (21.2×250 mm C8 "ZORBAX") eluting with water/ acetonitrile at 10 ml/minute and collecting 15 milliliter fractions. The appropriate fractions (as determined by UV at 210 nm) are combined and lyophilized to obtain the desired benzyl ether intermediate.

Part B. Bis benzyl derivative

To a solution of 28 milligrams (0.027 mmol) of Z'A in 200 microliters of dry pyridine is added sequentially 5 milligrams (0.041 mmol) of 4-dimethylaminopyridine and 10 milligrams of benzyl 2-isocyanatoacetate in 100 microliters of pyridine and the mixture stirred at room temperature under nitrogen for one hour. The mixture is concentrated in vacuo and then dissolved in acetonitrile/water. The product is isolated by preparative HPLC using water/acetonitrile as eluant at 10 ml/min and collecting 8 milliliter fractions to obtain the benzyl ether-ester protected derivative of the compound of formula (4) as a white solid.

Part C. Removal of the protecting groups 7 milligrams of the benzyl ether-ester obtained above is dissolved in 2.5 milliliters of 20/80 water/acetic acid. An equal weight of Pd-C is added and the reaction mixture stirred at room temperature over 1 atmosphere of hydrogen for 4 hours. At the end of this time the mixture is filtered and the solvent removed in vacuo. The concentrate was lyophilized to obtain the product of formula (4) as a white solid.

EXAMPLE 5

In an operation carried out in a manner similar to that described in Example 4, the compound of formula (5) may be prepared.

EXAMPLE 6

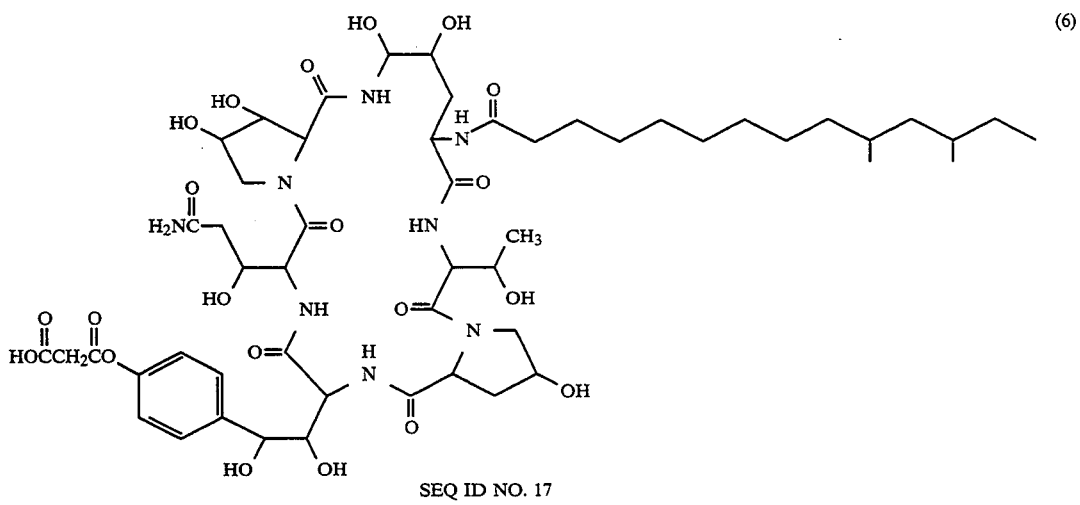

SEQ ID NO. 17 (6)

In reactions carried out in a manner similar to that described in the foregoing examples, 31 milligrams (1.1 eq) of 4-dimethylaminopyridine and 55 mg (1.1 eq) of monobenzyl malonic acid chloride are added sequentially to a solution of 250 milligrams (0.234 mmol) of Z'A in 2.5 ml of dry pyridine and the mixture stirred at room temperature. The reaction mixture is concentrated in vacuo, the residue dissolved in water/acetonitrile and purified by preparative reverse phase chromatography. Fractions containing the desired material are concentrated in vacuo to remove the acetonitrile and then lyophilized to obtain the benzyl ester.

The benzyl ester is then subjected to hydrogenolysis in ethanol over 10% palladium on carbon catalyst at room temperature for about 8 hours. Then the catalyst is filtered off and the filtrate concentrated to obtain compound of formula (6) as residue.

EXAMPLE 7

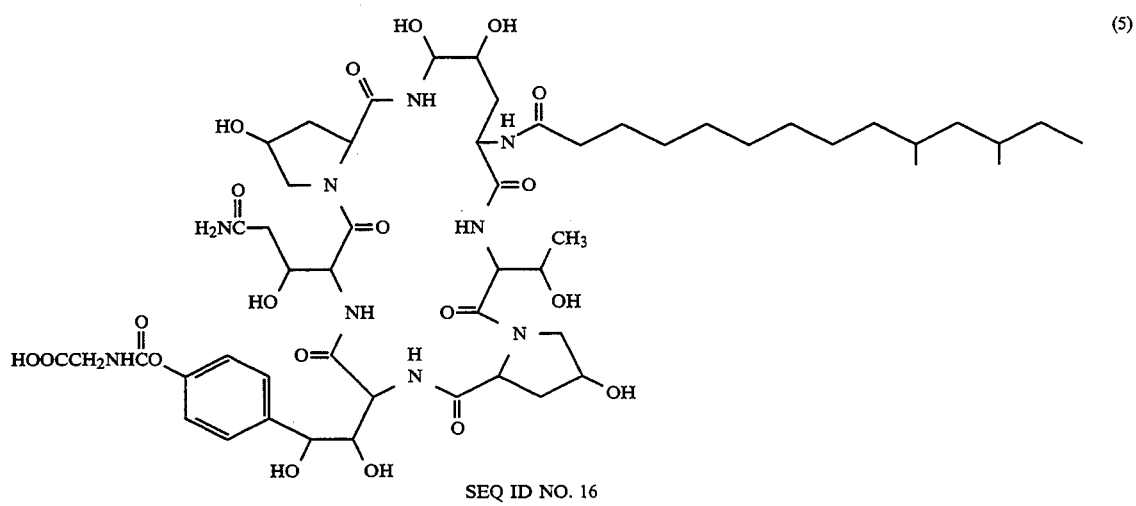

SEQ ID NO. 16 (5)

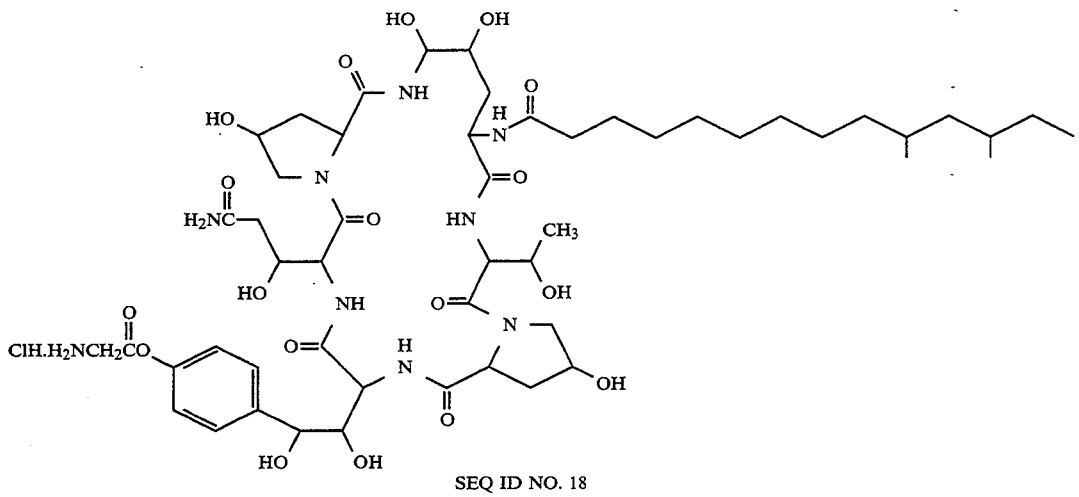

(7)

SEQ ID NO. 18

In a manner similar to that previously described, 31 milligrams (1.1 eq) of 4-dimethylaminopyridine and 126 milligrams (1.1 eq) of N-carboxybenzylglycine symmetrical anhydride are added sequentially to a solution 250 milligrams (0.234 mmol) of Z'B (benzyl ether) in 2.5 milliliters of dry pyridine and the mixture stirred at room temperature for 8 hours. It is then concentrated in vacuo, the residue dissolved in water/acetonitrile and purified by preparative reverse phase chromatography, eluting with water/acetonitrile.

The fractions containing the desired material are combined and concentrated, and then lyophilized to obtain purified carboxybenzyl protected glycyl ester.

The ester thus obtained is dissolved in 12 milliliters of ethanol containing an excess of anhydrous hydrochloric acid and 20 milligrams of 10% Pd-C catalyst is added and hydrogenation carried out at 1 atmosphere for 5 hours. At this time the catalyst is filtered off and the filtrate concentrated to obtain the compound of formula (7).

EXAMPLE 8

In similar operations, the following compounds are prepared:

| Compound No. | R | R' | |
|---|---|---|---|
| (8) | SO$_3$H | OH | SEQ ID NO. 19 |
| (9) | SO$_3$H | H | SEQ ID NO. 20 |
| (10) | COCH$_2$COOH | H | SEQ ID NO. 21 |
| (11) | CO(CH$_2$)$_2$NH$_2$.HCl | H | SEQ ID NO. 22 |
| (12) | COOCH$_2$NH$_2$.HCl | H | SEQ ID NO. 23 |
| (13) | PO(OH)(OCH$_3$) | H | SEQ ID NO. 24 |
| (14) | PO(OH)(OC$_2$H$_5$) | OH | SEQ ID NO. 25 |
| (15) | PO(OH)CH$_2$C$_6$H$_5$ | OH | SEQ ID NO. 26 |
| (16) | PO(OH)(OCH$_2$C$_6$H$_4$OCH$_3$(p)) | OH | SEQ ID NO. 27 |

In the following examples, the Arabic numeral designation refers to the formula of the compound in the example corresponding to the Arabic numeral.

EXAMPLE 9

1000 compressed tablets each containing 500 mg of Compound IA (of formula (1)) are prepared from the following formulation:

| Compound | Grams |
|---|---|
| Compound IA (or formula (1)) | 500 |
| Starch | 750 |
| Dibasic calcium phosphate hydrous | 5000 |
| Calcium stearate | 2.5 |

The finely powdered ingredients are mixed well and granulated with 107. starch paste. The granulation is dried and compressed into tablets.

EXAMPLE 10

1000 hard gelatin capsules, each containing 500 mg of Compound IB or formula (2) are prepared from the following formulation:

| Compound | Grams |
|---|---|
| Compound IB (or formula (2)) | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE 11

1000 hard gelatin capsules, each containing 500 mg of Compound are prepared from the following formulation:

| Compound | Grams |
|---|---|
| Compound IA (of formula (1)) | 500 |
| Starch | 250 |
| Lactose | 750 |
| Talc | 250 |
| Calcium stearate | 10 |

A uniform mixture of the ingredients is prepared by blending and used to fill two-piece hard gelating capsules.

EXAMPLE 12

1000 hard gelatin capsules, each containing 500 mg of compound of formula (3) are prepared from the following formulation:

| Compound | Grams |
| --- | --- |
| Compound of formula (3) | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE 13

250 ml of an injectable solution are prepared by conventional procedures having the following formulation:

| Dextrose | 12.5 g |
| --- | --- |
| Water | 250 mL |
| Compound IA (of formula (1)) | 400 mg |

The ingredients are blended and thereafter sterilized for use.

EXAMPLE 14

250 ml of an injectable solution are prepared by conventional procedures having the following formulation:

| Dextrose | 12.5 g |
| --- | --- |
| Water | 250 ml |
| Compound IB (of formula (2)) | 400 mg |

The ingredients are blended and thereafter sterilized for use.

EXAMPLE 15

An ointment suitable for topical application may be prepared by intimately dispersing 13 mg of Compound IA (formula (1)) in 1 g of commercially available polyethylene/hydrocarbon gel.

EXAMPLE 16

An injectable solution similar to that of Example 13 except that compound of formula (3) is substituted for compound of formula (1) is prepared.

EXAMPLE 17

1000 hard gelatin capsules, each containing mg of compound of formula (3) are prepared from the following formulation:

| Compound | Grams |
| --- | --- |
| Compound of formula (3) | 500 |
| Starch | 250 |
| Lactose | 750 |
| Talc | 250 |
| Calcium Stearate | 10 |

The components are uniformly blended and used to fill two-piece hard gelatin capsules.

EXAMPLE 18

An aerosol composition may be prepared having the following formulation:

| | Per Canister |
| --- | --- |
| Compound IA (formula (1)) | 24 mg |
| Lecithin NF Liquid Concentrated | 1.2 mg |
| Trichlorofluoromethane, NF | 4.026 g |
| Dichlorodifluoromethane, NF | 12.15 g |

Preparation of Starting Materials

The lipopeptide starting materials ZA and ZB are natural products produced by fermentation.

The starting compound Z may be obtained by aerobically cultivating *Zalerion arboricola* MF5533 ATCC 74030 first in one or several stages in an appropriate seed medium at temperatures in the range of from about 15° C. to about 30° C. for from 2 to 30 days, and thereafter in a fermentation production medium at temperatures in the range of from about 20° C. to about 40° C.

Representative seed medium is one of the following composition:

| | per/liter |
| --- | --- |
| Corn steep liquor | 5 g |
| D mannitol | 25 g |
| Glucose monohydrate | 10 g |
| Pharmamedia | 20 g |
| $KH_2PO_4$ | 9 g |
| $FeSO_4.7H_2O$ | 10 mg |
| $MnSO_4.4H_2O$ | 10 mg |
| $CuCl_2.2H_2O$ | 0.25 mg |
| $CaCl_2.2H_2O$ | 1 mg |
| $H_3BO_3$ | 0.56 mg |
| $(NH_4)_6Mo_7O_{24}.H_2O$ | 0.19 mg |
| $ZnSO_4.7H_2O$ | 2 mg |

A representative production medium is one of the following composition.

| | per/liter |
| --- | --- |
| D-Mannitol | 100 g |
| NZ-Amine type E* | 33 g |
| Fidco 8005 yeast extract | 10 g |
| $(NH_4)_2SO_4$ | 5 g |
| $KH_2PO_4$ | 9 g |
| P-2000 | 2 ml |

*Casein hydrolysate, Sheffield Products, Kraft, Inc.

Thereafter, the compound may be recovered from the cultivation medium by extracting from the medium with an alcoholic solvent, adjusting the alkanol extract to 50 percent water then employing chromatographic separations such as adsorbing on DIAION HP20 (Mitsubishi Chemical Industries) and eluting with methanol, followed by chromatographing on silica gel or on an HPLC column with ester/alcohol/water as mobile phase or by employing alternative method described in copending application Ser. No. 07/630,457.

The tetrabenzyl pyrophosphate employed in preparing the phosphate ester was obtained by a procedure modified from that described by Todd et al in J. Chem. Soc. 1953, 2257.

In such procedure, 10.0 grams of dibenzyl phosphate was added in one portion to 70 milliliters of tetrahydrofuran (THF) maintained at 20° C. in an atmosphere of nitrogen. The THF employed is previously dried over 3A sieves to a Karl Fischer assay of <50 µg/ml. To the THF solution of dibenzyl phosphate is added portionwise over a period of about 30 minutes a solution 3.9 grams of dicyclohexylcarbodiimide in 50 milliliters of THF while the temperature is maintained within a 5° range. Thereafter, the stirring is continued for about three hours at room temperature while monitoring by HPLC until no starting dibenzyl phosphate could be detected. The reaction solution is cooled to 0° C., filtered to remove the dicyclohexylurea byproduct and the organic solution concentrated under reduced pressure (0.10 atm, 23° C.) to dryness to obtain the desired tetrabenzyl pyrophosphate.

---

What is claimed is:

1. A compound having the formula

-continued

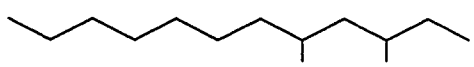

wherein R' is a phosphono, sulfo or acyl radical having a charged group at neutral pH, wherein
(1) "phosphono" is a radical or group derived from and remaining after an OH of the phosphoric acid or monoester of phosphoric acid has reacted with the hydrogen of the phenolic group on the lipopeptide and is represented by $-PO_3AH$ wherein A is H, $C_1-C_6$ alkyl, phenyl or substituted phenyl in which the substituent is alkyl, alkyloxy, alkylthio, or alkylamino, or a cation salt thereof;
(2) "sulfo" is a radical group derived from and remaining after an OH of the sulfuric acid has reacted with the hydrogen of the phenolic group on the lipopeptide and is represented by $-SO_3H$ or cation salt thereof;
(3) "acyl" is a radical or group derived from a carboxylic acid and further defined as follows:
 (i) $COC_nH_{2n}CO_2H$ wherein n is 1 to 6, or a cation malt thereof;
 (ii) $CONAC_nH_{2n}CO_2H$ where A is as defined in (1) and n is 1 to 6, or a cation salt thereof;
 (iii) $COOC_nH_{2n}CO2H$ wherein n is 1 to 6, or a cation malt thereof;
 (iv) $CONA(CHB)CO_2H$ wherein A is as defined in (1) and B is a residue of an amino acid, or a cation salt thereof;
 (v) $COCHBNR_1R_2$ wherein B is a residue of an amino acid, $R_1$ and $R_2$ independently are H, $C_1-C_6$ alkyl, or phenyl, or an acid addition salt thereof;
 (vi) $CONAC_nH_{2n}NR_1R_2$ wherein A is as defined in (1), $R_1$ and $R_2$ independently are as defined in (v), n is 2 to 6, or an acid addition salt thereof;
 (vii) $COOC_nH_{2n}R_1R_2$ wherein $R_1$ and $R_2$ independently are as defined in (v), n is 2 to 6, or an acid addition salt thereof;
 (viii) $COC_nH_{2n}NR_1R_2$ wherein $R_1$ and $R_2$ independently are as defined in (v), n is 1 to 6 or an acid addition salt thereof.

2. A compound according to claim 1 wherein R' is phosphono having the formula $PO_3AH$ wherein A is H, $C_1-C_6$ alkyl, phenyl or substituted phenyl wherein the substituent may be alkyl, alkyloxy, alkylthio, or alkylamino or a cation salt thereof.

3. A compound according to claim 1 wherein R' is sulfo having the formula $SO_3H$, or a cation salt thereof.

4. A compound according to claim 1 wherein R' is acyl selected from the group consisting of:
(i) $COC_nH_{2n}CO_2H$ wherein n is 1 to 6 or a cation salt thereof;
(ii) $CONAC_nH_{2n}CO_2H$ wherein A is as defined in (1), n is 1 to 6, or a cation salt thereof;
(iii) $COOC_nH2nCO_2H$ wherein n is 1 to 6, or a cation salt thereof;
(iv) $CONA(CHB)CO_2H$ wherein B is a residue of an amino acid, or a cation salt thereof;
(v) $COCHBNR_1R_2$ wherein B is a residue of an amino acid, $R_1$ and $R_2$ independently are H, $C_1-C_6$ alkyl, and phenyl, and acid addition salts thereof;
(vi) $CONAC_nH_{2n}NR_1R_2$ wherein A is as defined in (1), $R_1$ and $R_2$ independently are as defined in (v), n is 2 to 6, and acid addition salts thereof;
(vii) $COOC_nH_{2n}R_1R_2$ wherein $R_1$ and $R_2$ independently are as defined in (v), n is 2 to 6, and acid addition salts thereof; and
(viii) $COC_nH_{2n}NR_1R_2$ wherein $R_1$ and $R_2$ independently are as defined in (v), n is 1 to 6 and acid addition salts thereof.

5. A compound according to claim 1 having the formula

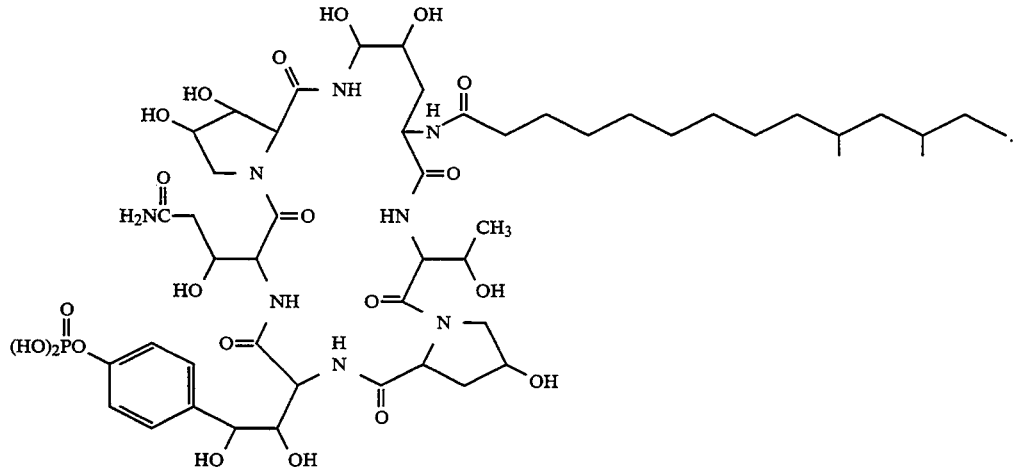

6. An antibiotic composition comprising a compound of claim 1 in admixture with a pharmaceutically acceptable carrier.

7. A composition according to claim 6 wherein the carrier is an aqueous medium.

8. A method for inhibiting or treating mycotic infections comprising administering a therapeutic amount of a compound of claim 1.

9. A method of inhibiting or alleviating the infection caused by Pneumocystis carinii in an infected or immunosuppressed patient in need thereof comprising administering a therapeutic amount of the compound of claim 1.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa  Thr  Xaa  Xaa  Xaa  Xaa
    1                      5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Xaa  Thr  Xaa  Xaa  Xaa  Xaa
    1                      5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Xaa  Thr  Xaa  Xaa  Xaa  Xaa
    1                      5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Xaa Thr Xaa Xaa Xaa Xaa
1             5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Xaa Thr Xaa Xaa Xaa Xaa
1             5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

Xaa Thr Xaa Xaa Xaa Xaa
1             5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

Xaa Thr Xaa Xaa Xaa Xaa
1             5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

```
Xaa Thr Xaa Xaa Xaa Xaa
1               5
```

( 2 ) INFORMATION FOR SEQ ID NO:9:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

```
Xaa Thr Xaa Xaa Xaa Xaa
1               5
```

( 2 ) INFORMATION FOR SEQ ID NO:10:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
Xaa Thr Xaa Xaa Xaa Xaa
1               5
```

( 2 ) INFORMATION FOR SEQ ID NO:11:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

```
Xaa Thr Xaa Xaa Xaa Xaa
1               5
```

( 2 ) INFORMATION FOR SEQ ID NO:12:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

```
Xaa Thr Xaa Xaa Xaa Xaa
1               5
```

( 2 ) INFORMATION FOR SEQ ID NO:13:

( i ) SEQUENCE CHARACTERISTICS:
  ( A ) LENGTH: 6 amino acids
  ( B ) TYPE: amino acid
  ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:13:

Xaa Thr Xaa Xaa Xaa Xaa
1               5

( 2 ) INFORMATION FOR SEQ ID NO:14:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:14:

Xaa Thr Xaa Xaa Xaa Xaa
1               5

( 2 ) INFORMATION FOR SEQ ID NO:15:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:15:

Xaa Thr Xaa Xaa Xaa Xaa
1               5

( 2 ) INFORMATION FOR SEQ ID NO:16:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:16:

Xaa Thr Xaa Xaa Xaa Xaa
1               5

( 2 ) INFORMATION FOR SEQ ID NO:17:

( i ) SEQUENCE CHARACTERISTICS:
    ( A ) LENGTH: 6 amino acids
    ( B ) TYPE: amino acid
    ( D ) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:17:

Xaa Thr Xaa Xaa Xaa Xaa
1               5

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:18:

Xaa Thr Xaa Xaa Xaa Xaa
1               5

(2) INFORMATION FOR SEQ ID NO:19:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:19:

Xaa Thr Xaa Xaa Xaa Xaa
1               5

(2) INFORMATION FOR SEQ ID NO:20:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:20:

Xaa Thr Xaa Xaa Xaa Xaa
1               5

(2) INFORMATION FOR SEQ ID NO:21:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (iii) HYPOTHETICAL: NO (iv) ANTI-SENSE: NO ( x i ) SEQUENCE DESCRIPTION: SEQ ID NO:21:

Xaa Thr Xaa Xaa Xaa Xaa
1               5

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:22:

Xaa Thr Xaa Xaa Xaa Xaa
1               5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

Xaa Thr Xaa Xaa Xaa Xaa
1               5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:24:

Xaa Thr Xaa Xaa Xaa Xaa
1               5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:25:

Xaa Thr Xaa Xaa Xaa Xaa
1               5

(2) INFORMATION FOR SEQ ID NO:26:

(i) SEQUENCE CHARACTERISTICS:
    (A) LENGTH: 6 amino acids
    (B) TYPE: amino acid
    (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:26:

Xaa  Thr  Xaa  Xaa  Xaa  Xaa
  1                 5

(2) INFORMATION FOR SEQ ID NO:27:

(i) SEQUENCE CHARACTERISTICS:
    (A) LENGTH: 6 amino acids
    (B) TYPE: amino acid
    (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:27:

Xaa  Thr  Xaa  Xaa  Xaa  Xaa
  1                 5

(2) INFORMATION FOR SEQ ID NO:28:

(i) SEQUENCE CHARACTERISTICS:
    (A) LENGTH: 6 amino acids
    (B) TYPE: amino acid
    (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:28:

Xaa  Thr  Xaa  Xaa  Xaa  Xaa
  1                 5

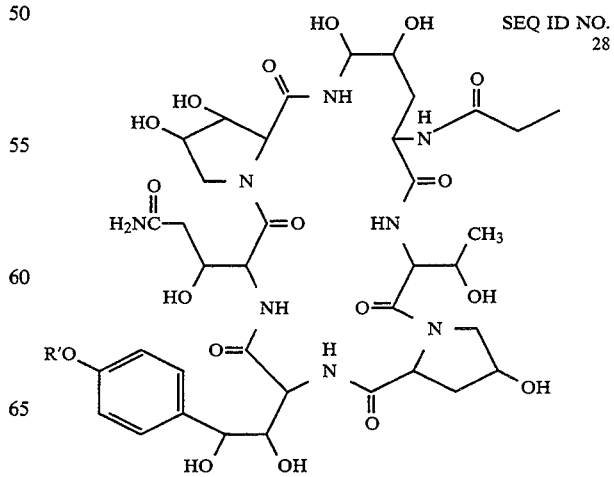

SEQ ID NO. 28